US009475634B2

(12) United States Patent
Prischak

(10) Patent No.: US 9,475,634 B2
(45) Date of Patent: Oct. 25, 2016

(54) SPRAY DISPENSING CUP

(76) Inventor: Nicholas Joseph Prischak, Erie, PA (US)

( * ) Notice: Subject to any disclaimer, the term of this patent is extended or adjusted under 35 U.S.C. 154(b) by 1327 days.

(21) Appl. No.: 13/308,960

(22) Filed: Dec. 1, 2011

(65) Prior Publication Data

US 2012/0138699 A1 Jun. 7, 2012

Related U.S. Application Data

(60) Provisional application No. 61/418,511, filed on Dec. 1, 2010.

(51) Int. Cl.

| | |
|---|---|
| ***B05B 7/00*** | (2006.01) |
| ***B08B 3/04*** | (2006.01) |
| ***B65D 83/14*** | (2006.01) |
| ***B65D 83/00*** | (2006.01) |
| ***A61H 33/04*** | (2006.01) |
| ***A61M 35/00*** | (2006.01) |
| ***B65D 83/20*** | (2006.01) |
| ***B65D 83/28*** | (2006.01) |
| ***B65D 83/40*** | (2006.01) |
| *B05B 1/26* | (2006.01) |

(52) U.S. Cl.

CPC ............. *B65D 83/205* (2013.01); *B65D 83/28* (2013.01); *B65D 83/40* (2013.01); *B05B 1/262* (2013.01)

(58) Field of Classification Search

CPC .... B65D 83/205; B65D 83/16; B65D 83/00; A61H 33/04; B05B 7/00; A61M 35/00

USPC ............ 401/261–265, 190, 188, 11, 146, 88, 401/552; 222/150, 152, 153, 383.1, 153.13, 222/153.01; 206/229; 239/589

See application file for complete search history.

(56) References Cited

U.S. PATENT DOCUMENTS 3,154,615 A * 10/1964 Cooprider ..................... 264/242
3,256,549 A 6/1966 Evesque
3,306,252 A * 2/1967 Knight ................ A61M 35/003 118/710
3,744,678 A * 7/1973 Beres ..................... B65D 83/30 222/205
3,759,431 A * 9/1973 Vos ...................... B65D 83/206 222/402.21
3,792,802 A 2/1974 Gores
3,841,532 A * 10/1974 Gores .................... B65D 83/28 222/205
3,865,283 A 2/1975 Hayes
3,887,115 A * 6/1975 Petterson ............... B65D 83/30 132/320
3,917,127 A 11/1975 Berenstain
3,936,000 A * 2/1976 Weyn ..................... B65D 83/30 222/182
4,154,375 A * 5/1979 Bippus .......................... 222/325
4,226,340 A * 10/1980 Troesch ............... B65D 83/386 222/183
4,407,481 A * 10/1983 Bolton .................... G01F 11/38 222/402.2
4,420,099 A * 12/1983 Pizzurro ................ B65D 83/30 222/182
4,986,453 A * 1/1991 Lina et al. ................. 222/321.2
5,335,832 A * 8/1994 de Laforcade ....... B65D 83/206 222/402.13
5,551,603 A * 9/1996 Woodruff ............ B05B 11/0048 222/325

(Continued)

*Primary Examiner* — Mark A Laurenzi
*Assistant Examiner* — Thomas M Abebe
(74) *Attorney, Agent, or Firm* — Bachman & LaPointe, P.C.

(57) ABSTRACT

A spray apparatus has a container and a nozzle assembly. The nozzle assembly includes a cup member and a retention ring. The cup member has a central concave surface and a hole open to the central concave surface. A conduit extends downward below the hole and cooperates with the container to allow depression of the cup member from a first condition to a second condition to, in turn, pass product from the container out the hole. The retention ring has an inner portion secured to the container and an outer portion cooperating with the sidewall to resist upward movement of the sidewall of the cup member beyond the first condition.

19 Claims, 8 Drawing Sheets

(56) References Cited

U.S. PATENT DOCUMENTS

| | | | | |
|---|---|---|---|---|
| 5,567,073 | A | 10/1996 | de Laforcade et al. | |
| 5,593,064 | A * | 1/1997 | Meshberg | B05B 11/0032 222/153.11 |
| 6,053,898 | A * | 4/2000 | Ostrow | A61M 35/00 222/175 |
| 6,113,008 | A * | 9/2000 | Arsenault | A61M 35/003 222/402.13 |
| 6,123,234 | A * | 9/2000 | Lai | B05B 11/0005 222/321.7 |
| 6,158,674 | A * | 12/2000 | Humphreys | B05B 1/14 222/321.6 |
| 6,412,671 | B1 * | 7/2002 | Riley | B65D 83/303 222/402.1 |
| 6,491,187 | B2 * | 12/2002 | Walters | B65D 83/206 222/173 |
| 6,695,171 | B2 * | 2/2004 | Walters | B05B 11/3059 222/153.13 |
| 7,044,337 | B1 | 5/2006 | Kou | |
| 7,137,536 | B2 * | 11/2006 | Walters | B65D 83/206 222/39 |
| 7,500,583 | B1 | 3/2009 | Cox | |
| 7,578,388 | B2 * | 8/2009 | O'Connell | B05C 17/002 206/223 |
| 7,628,298 | B2 * | 12/2009 | Dewig | B65D 83/40 220/915 |
| 7,784,645 | B2 * | 8/2010 | Carta | 222/153.01 |
| 7,784,647 | B2 * | 8/2010 | Tourigny | B05B 11/3052 222/205 |
| 7,841,793 | B2 * | 11/2010 | Ramet | A45D 34/04 132/320 |
| 7,871,217 | B2 * | 1/2011 | Kennedy | A45D 34/04 222/321.7 |
| 7,905,673 | B2 * | 3/2011 | Swaile | A61K 8/046 222/402.1 |
| 7,963,425 | B2 * | 6/2011 | O'Connell White | G09F 23/00 206/223 |
| 7,984,832 | B2 * | 7/2011 | Pivonka | A45D 34/04 222/205 |
| 8,308,030 | B2 * | 11/2012 | Drugeon | A45D 34/02 215/272 |
| 8,479,752 | B2 * | 7/2013 | Duffield | B65D 83/285 134/104.2 |
| 8,496,014 | B2 * | 7/2013 | Bown | B08B 3/026 134/104.2 |
| 8,646,661 | B2 * | 2/2014 | Paine | B65D 83/546 222/108 |
| 8,695,896 | B2 * | 4/2014 | Tu | B05B 11/0056 141/113 |
| 8,733,599 | B2 * | 5/2014 | Hornland | B65D 83/205 222/135 |
| 8,794,176 | B2 * | 8/2014 | Schann | B05B 15/045 118/300 |
| 2005/0158116 | A1 * | 7/2005 | Belansky | A46B 11/001 401/270 |
| 2006/0253089 | A1 * | 11/2006 | Lin | A61F 9/0026 604/301 |
| 2007/0041774 | A1 * | 2/2007 | Tourigny | B65D 83/20 401/11 |
| 2008/0006718 | A1 * | 1/2008 | Junkel | A45F 3/16 239/333 |
| 2011/0031281 | A1 * | 2/2011 | Leleu | B05B 11/3047 222/321.1 |
| 2014/0190995 | A1 * | 7/2014 | Von Schuckmann | B05B 11/0013 222/256 |

* cited by examiner

SPRAY DISPENSING CUP

CROSS-REFERENCE TO RELATED APPLICATION

Benefit is claimed of U.S. Patent Application Ser. No. 61/418,511, filed Dec. 1, 2010, and entitled "Spray Dispensing Cup", the disclosure of which is incorporated by reference herein in its entirety as if set forth at length.

BACKGROUND OF THE INVENTION

The invention relates to pressurized spray containers. More particularly, the invention relates to spray dispensing of personal care compositions such as deodorants, antiperspirant, and the like.

A typical spray container or bottle takes the form of a metallic can having a top-mounted valve assembly. Exemplary valve assemblies are actuated by depressing a spray nozzle mounted at the top of the valve assembly to open the valve and create a pathway for contents of the can to exit under pressure. In some containers, the contents are contained within a bag and the pressurant is within the can surrounding the bag. In some containers, the valve inlet is formed as or connected to a dip tube which extends down into a body of liquid in the can. In bag-less variations, the headspace of the can above the liquid contains the pressurant in normal use. Common valve assemblies include male type and female type. In a male valve assembly, a stem extends upward from the valve and is received in the nozzle. Depression of the nozzle acts to depress the stem to open the valve. In female valve assemblies, the nozzle includes a stem which is received in the valve assembly and similarly actuates spraying.

In a traditional spray nozzle, the user depresses a top of the nozzle with the user's index finger and sprays discharge from a lateral outlet in the nozzle. The spraying action may dispense the product in a pattern that leaves a significant portion of the product to miss the target area (e.g., an underarm area of the person applying the spray).

SUMMARY OF THE INVENTION

One aspect of the disclosure involves a spray apparatus having a container and a nozzle assembly. The nozzle assembly includes a cup member and a retention ring. The cup member has a central concave surface and a hole open to the central concave surface. A conduit extends downward below the hole and cooperates with the container to allow depression of the cup member from a first condition to a second condition to, in turn, pass product from the container out the hole. The retention ring has an inner portion secured to the container and an outer portion cooperating with the sidewall to resist upward movement of the sidewall of the cup member beyond the first condition.

Another aspect of the disclosure involves a method for operating a spray apparatus comprising a container and a nozzle assembly. The nozzle assembly further includes a cup member having a peripheral lip portion surrounding a central concavity. The lip portion of the cup member is contacted with skin of the user so that the skin and the cup member define a volume. The cup member is depressed to discharge a spray of the product from a hole into the volume and onto the skin. The depressing may comprise applying pressure/force between the container and the skin. The product may comprise at least one of an antiperspirant and a deodorant and the skin may be along an underarm region.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
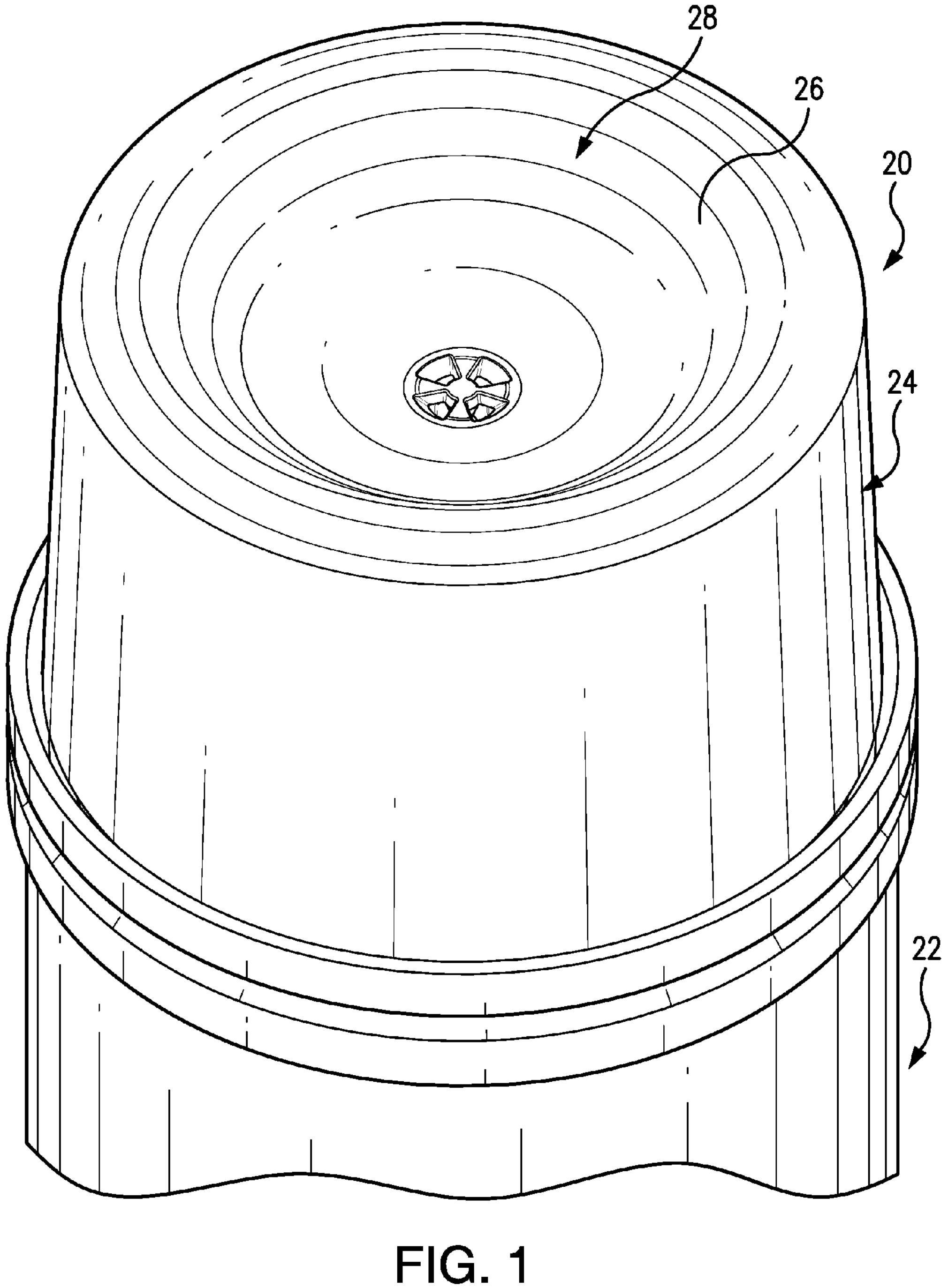
FIG. 1 is a view of a top portion of a spray container with overcap removed.

FIG. 1 shows a nozzle assembly 20 on a container (bottle) 22. The exemplary bottle comprises a metallic can. The exemplary can comprises any of a number of prior art or yet-developed can configurations. However, other configurations may be used. The exemplary can configuration (FIG. 2) comprises a metallic sidewall 200 of nominal right circular cylindrical configuration (e.g., formed of sheet steel and soldered (or otherwise closed) along a longitudinal seam (not shown)). The exemplary can further comprises a single-piece bottom/base 202 formed of a metal (e.g., stainless steel) stamping and crimped (at an annular joint or crimp 204) to a lower rim portion of the sidewall. The exemplary bottle further comprises a top 206. The exemplary top is formed of a multi-piece assembly comprising an outer member 208 and an inner member 210 (formed as a valve cup-discussed below). Both exemplary outer and inner members are metal (e.g., stainless steel) stampings with the outer member secured at its outer periphery to an upper rim portion of the sidewall 200 at an annular joint or crimp 212. At its inner peripheral (inner diameter) the outer member 208 is secured to an outer peripheral (outer diameter) portion of the valve cup 210 at an annular joint or crimp 214. The various crimps may, themselves, be soldered or otherwise sealed/secured in addition to the mechanical interlocking provided by the crimping action.

A valve assembly 220 may be mounted to the top 206 (e.g., to the valve cup 210) within the can. In various implementations, a dip tube 222 may extend into the can from the valve assembly. A lower end of the dip tube extends within a body 224 of the liquid product to be dispensed when the container is upright. An upper end portion of the dip tube may mate directly or indirectly with the valve structure. The dip tube may be within a bag (not shown) containing the body 224 of liquid contents (e.g., deodorant and/or antiperspirant) to be dispensed. Other configurations may eliminate the dip tube.

Figure 2:
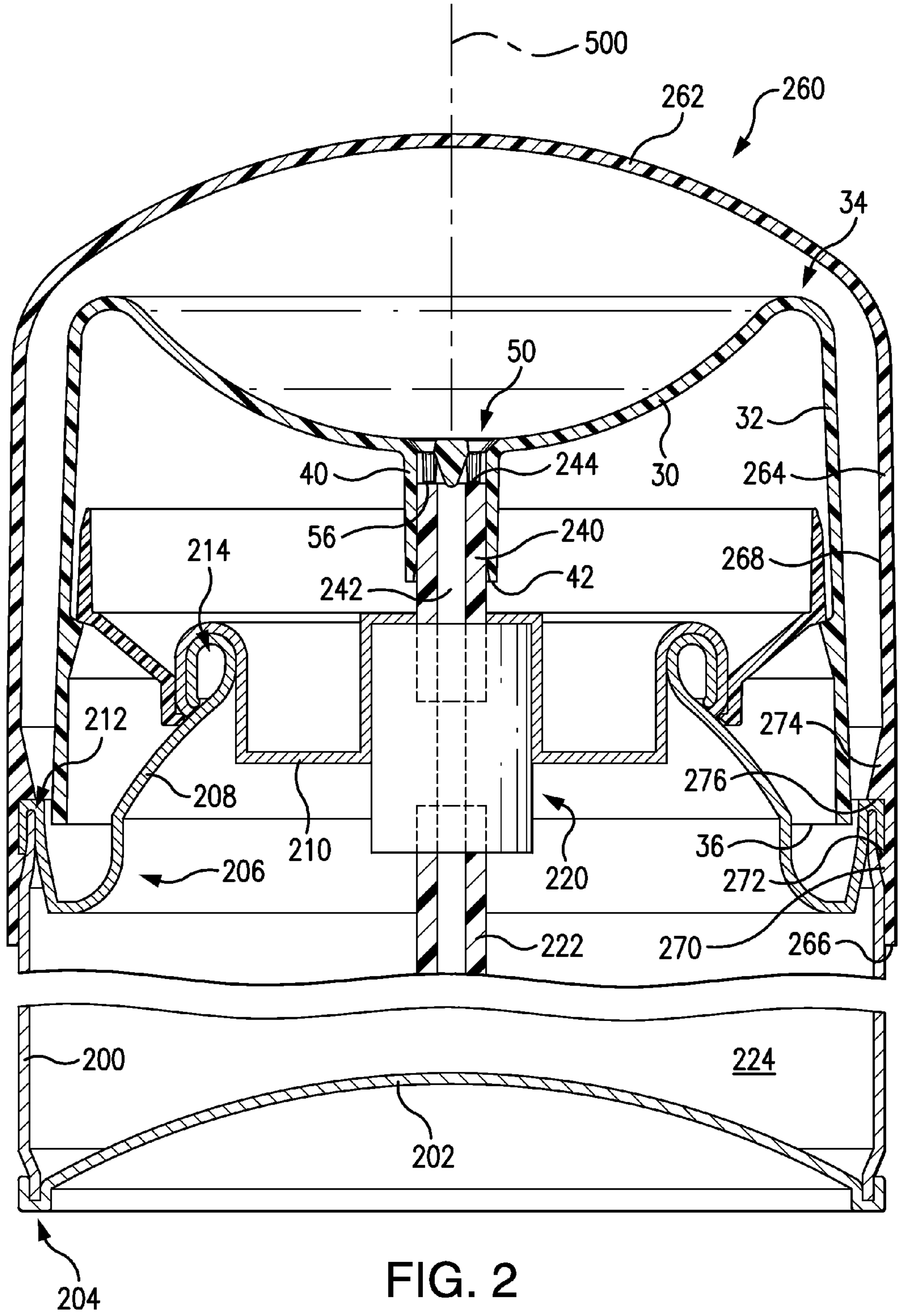
FIG. 2 is a central vertical/longitudinal section view of the container with overcap.

The exemplary valve is shown as a conventional spring-biased male valve having an upwardly projecting outlet stem 240 having a central passageway 242 and extending to an upper rim 244. FIG. 2 shows a closed/extended condition of the valve stem. The valve stem 240 is depressible against spring (not shown) bias into a depressed/opened condition (discussed below) to establish communication from the body of container contents through the nozzle.

As is discussed below, FIG. 2 further includes a removable domed overcap 260 (e.g., a single piece of molded plastic such as polypropylene). Again, the domed overcap may be of conventional or other configuration. The exemplary overcap includes an outwardly convex upper web 262 and a cylindrical sidewall 264 depending from a junction with the upper web to a lower rim 266. Along an interior surface 268, the sidewall 264 bears an inwardly projecting lower annular bead/barb 270 having an upwardly facing locking shoulder surface 272 which, when installed, engages an underside of the joint/crimp 212 to resist vertical extraction/removal of the overcap. Above the bead/barb 270, is an oppositely directed bead/barb 274 having a downwardly facing locking shoulder surface 276 for engaging the upper rim of the joint 212 to resist further downward movement below the installed condition of the overap. The overcap is forcibly removable and reinstallable without damage.

FIG. 1 show the nozzle assembly 20 as including a top member or cup member 24 (e.g., a single piece of molded plastic such as polypropylene) having a concave upper surface portion 26 defining a central well or concavity 28. The upper surface 26 is along a cup/bowl structure 30 (FIG. 2). An outer sidewall 32 depends from a junction 34 with the bowl structure. Junction 34 defines an upper lip/rim of the top/cup member 24. The sidewall 32 depends to a lower rim 36.

Figure 3:
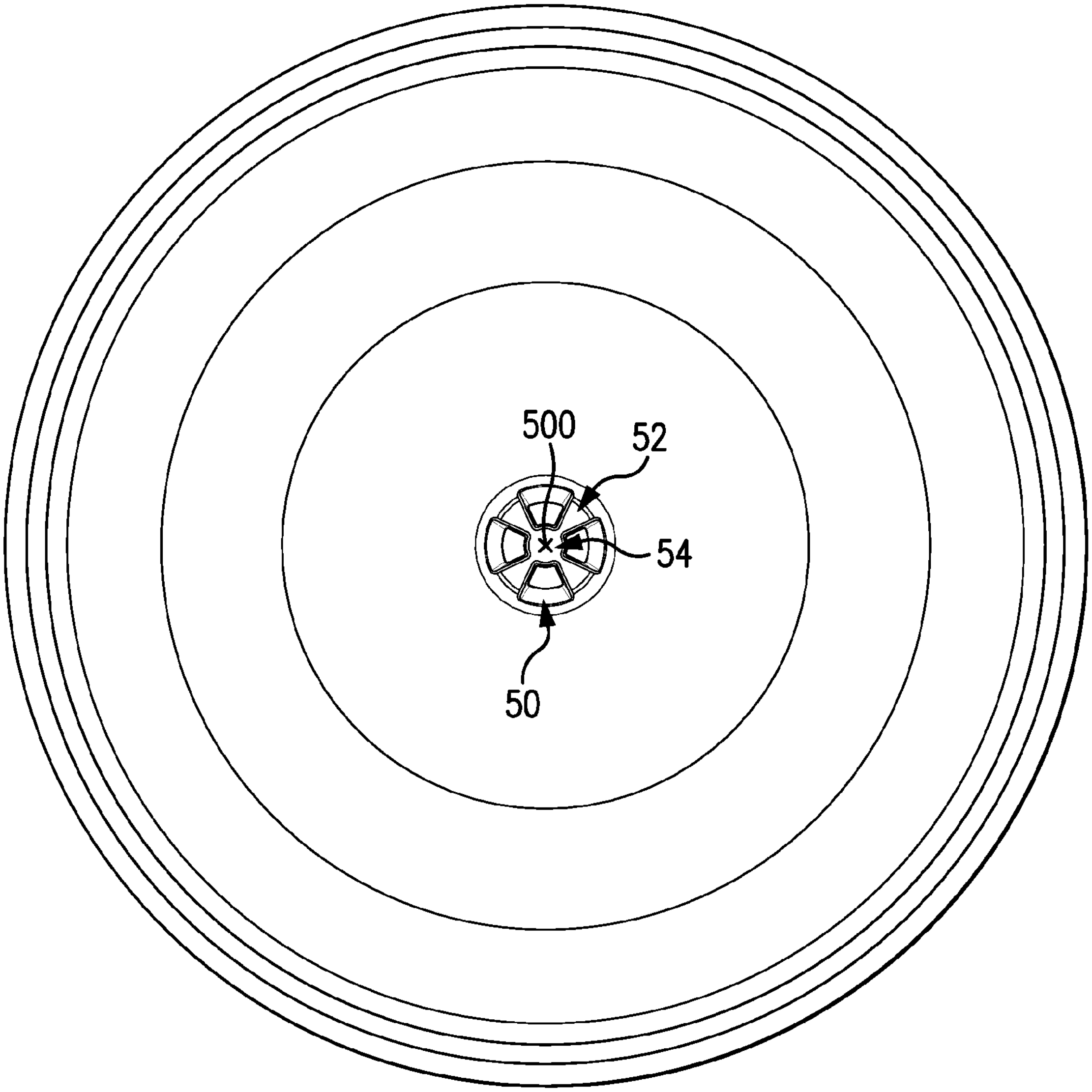
FIG. 3 is a top view of the container of FIG. 1.

The top/cup member includes a conduit or sleeve structure 40 depending centrally from the bowl structure to a lower rim 42 to receive an upper portion of the stem 240. Near the rim 42, the inner surface of the sleeve 40 has a slight bevel/chamfer to guide insertion/reception of the stem during assembly. The top/cup member 24 includes an opening (outlet) in the form of a plurality of openings/apertures 50. FIG. 3 shows four apertures 50 positioned/oriented at even angular intervals about a central vertical axis/centerline 500. The apertures 50 are separated by radial webs 52 which extend inward to a centerbody 54. The webs 52 have undersides 56 abutting the rim surface 244 of the stem.

Figure 4:
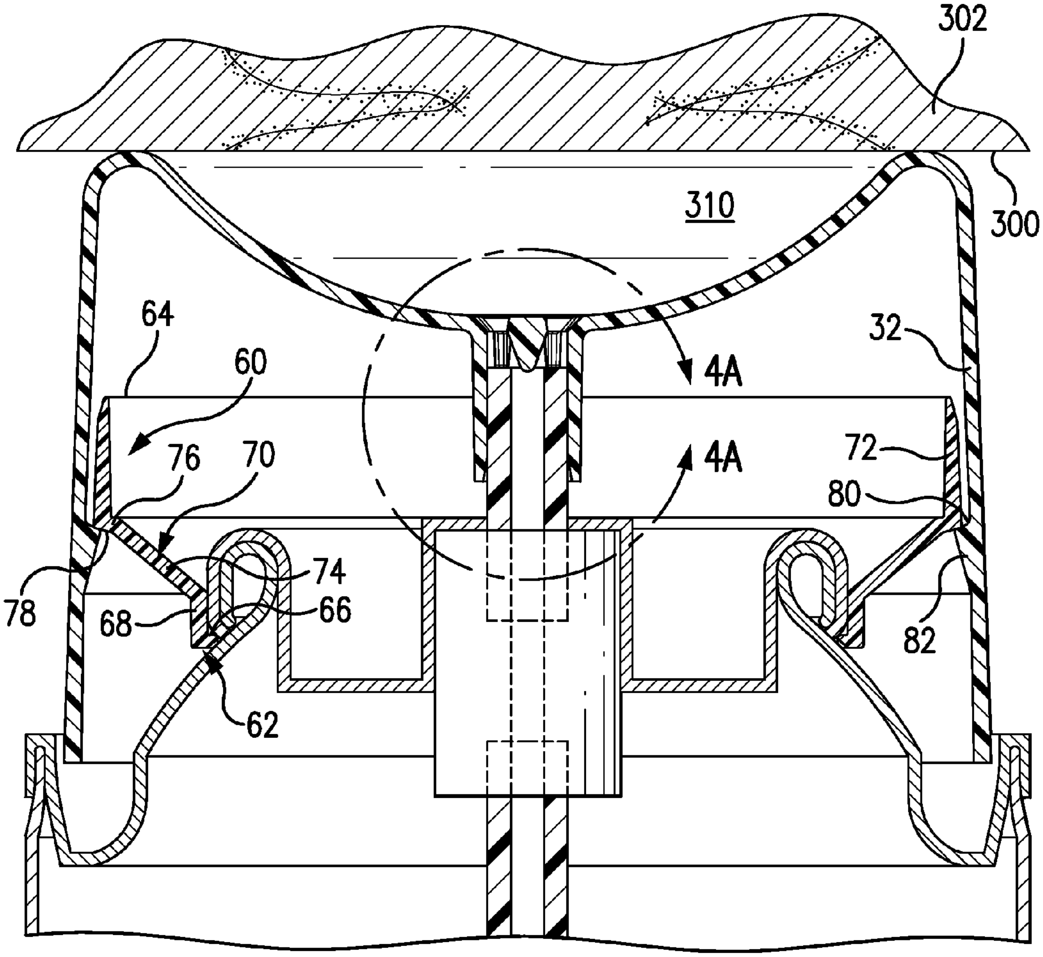
FIG. 4 is a view of the container engaged to the skin of a user.
Figure 4A:
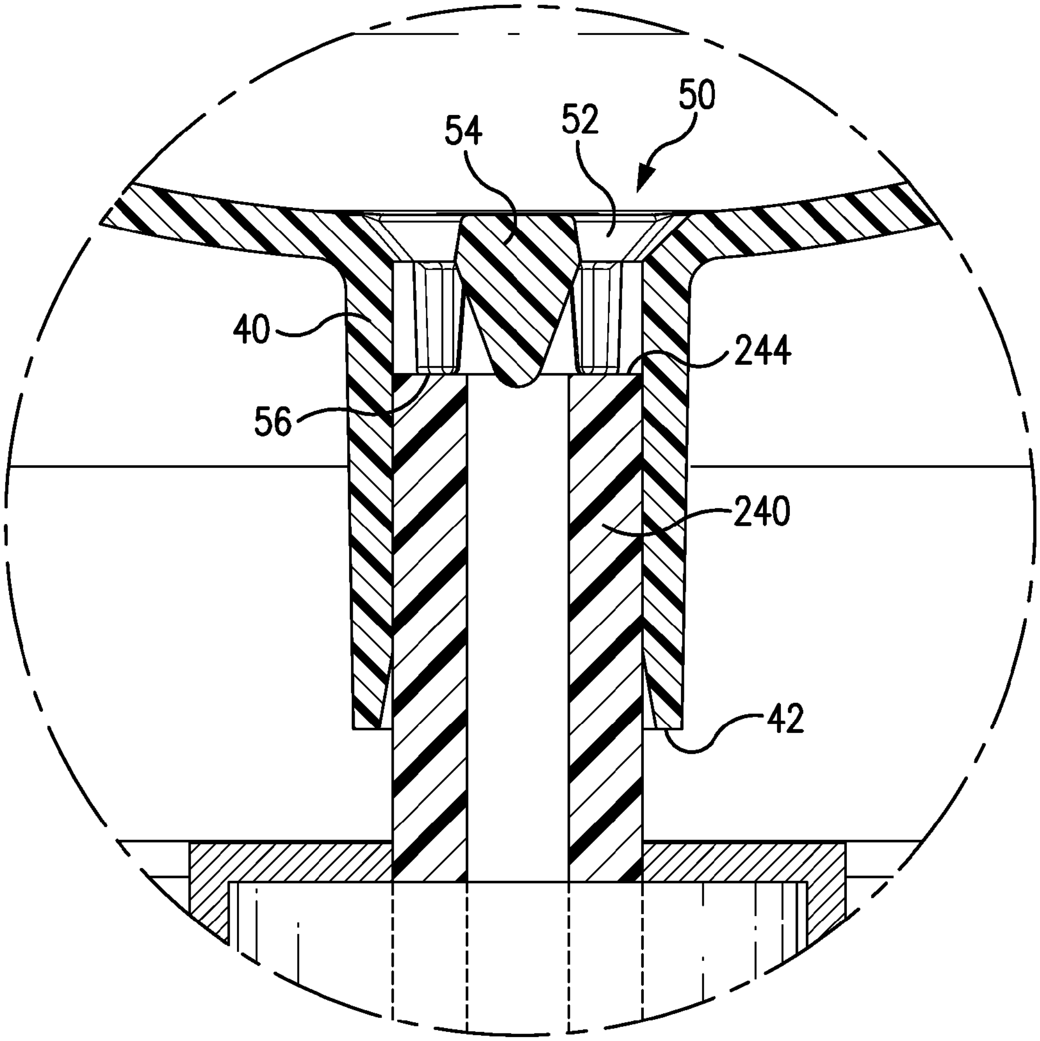
FIG. 4A is a an enlarged view of an oulet region of the container of FIG. 4, taken along line 4A-4A.

FIG. 4 shows the container with the overcap removed and the rim/lip 34 brought into engagement with a surface 300 of the skin 302 of the user (e.g., along an underarm area). The concave surface of the top member and the adjacent portion of the rim along with the enclosed skin surface define a volume 310 into which the product is sprayed.

FIG. 4 further shows the nozzle assembly 20 as having a retention ring 60 (e.g., a single piece of molded plastic such as polypropylene) extending from a lower rim portion 62 to an upper rim portion 64.

The exemplary retention ring mates with the inner junction (crimp) 214 of the container top. To do this, it may have an annular barb/bead 66 engaging an underside of the crimp 214. The barb/bend 66 may be along the inner diameter (ID) surface of a lower sleeve/collar portion 68 of the retention ring. A shoulder 70 may extend radially outward from an upper end of the collar portion 68 to an outer sidewall portion 72 whose outer diameter (OD) surface closely cooperates with the inner diameter (ID) surface of the top member sidewall 32 to guide movement of the top member between its conditions. In the exemplary embodiment, the shoulder 70 has a generally frustoconical main portion 74 with a more radial outer portion 76 at the lower end of the sidewall 72. An underside 78 of this more radial outer portion 76 may cooperate with the upward-facing underside 80 of the engagement end of an inwardly directed barb/bead 82 of the top member sidewall 32 to prevent or otherwise resist movement of the top member beyond its extended position. In the extended position, the spring bias of the valve may be pushing the stem 240 upward. The force of the stem is transferred via its rim to the undersides of the webs 52. This force is transferred via the barb/beads 82 to the retention ring which, in turn, transfers the force through the barb/bead 66 to the can.

Figure 5:
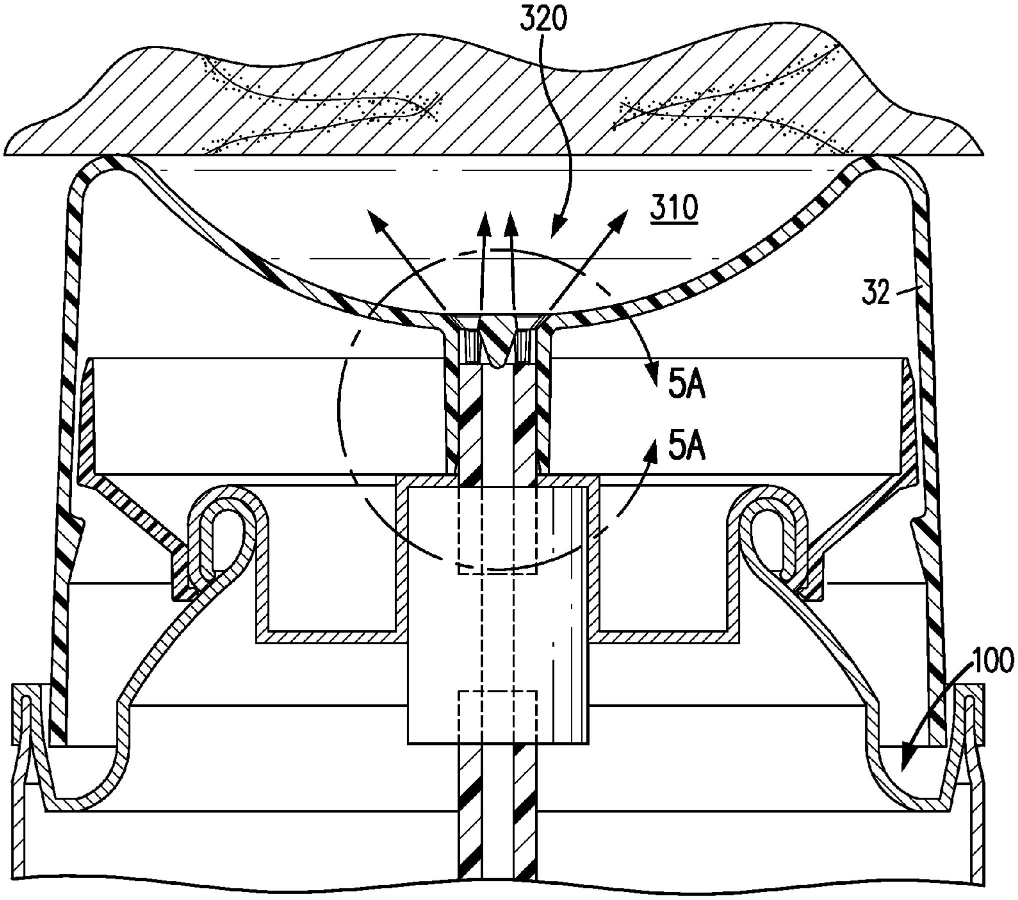
FIG. 5 is a view of the container of FIG. 4 in a discharging condition.
Figure 5A:
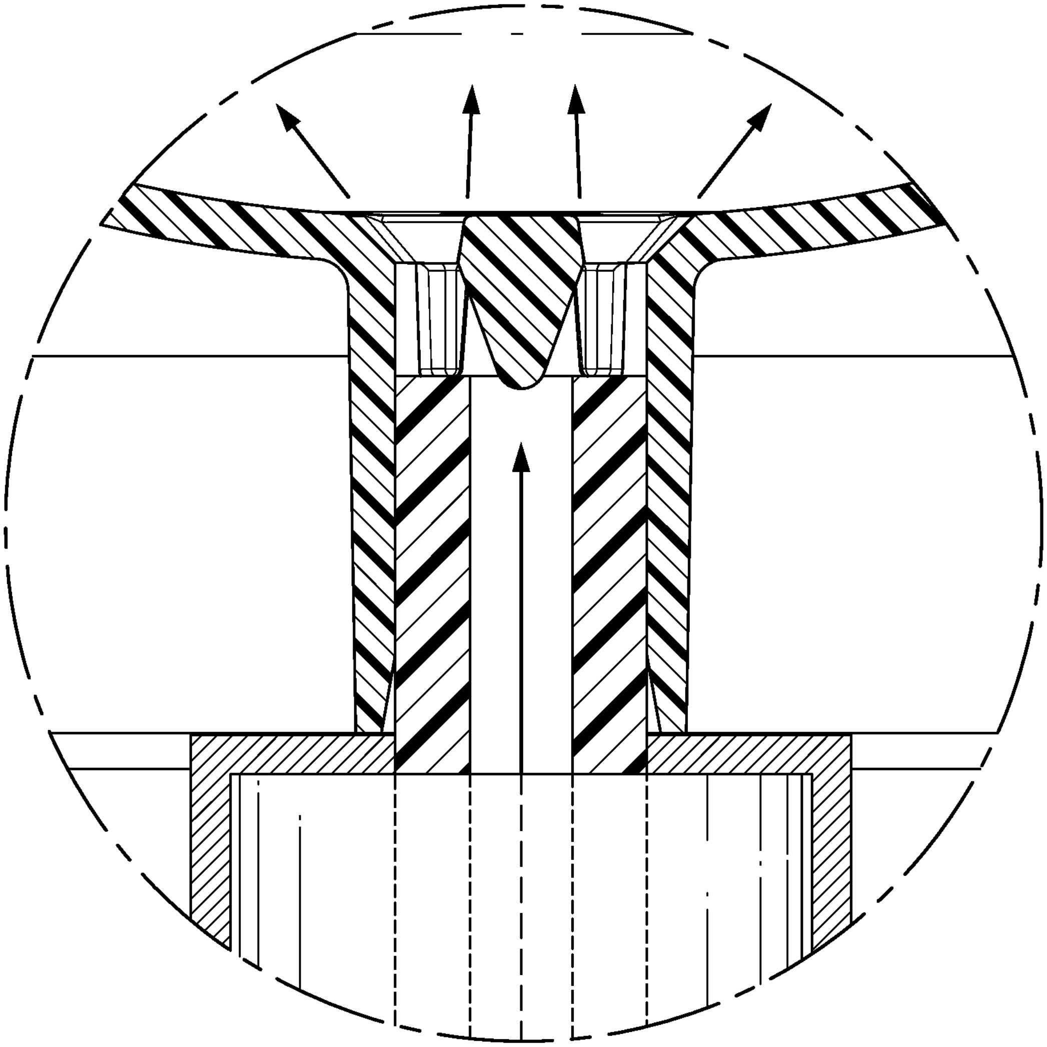
FIG. 5A is an enlarged view of an outlet portion of the container of FIG. 5, taken along line 5A-5A.

In use, the overcap is extracted/removed and the top member rim 34 may be brought into engagement with the user's skin (e.g., along the underarm). The container may be pressed against the skin causing the top member to press downward relative to the container and depress the top member and valve stem to a depressed/opened condition of FIG. 5 and thereby opening the valve and dispensing sprays 320 of the product into the volume 310 between the concave surface and the adjacent skin. This depressing may cause the lower end portion of the top member sidewall 32 to enter (or pass more deeply into) an annular recess 100 in the outer member. The top member may be dimensioned so that the rim 36 can contact the channel when the valve is fully depressed. This again provides a more rigid feel. When pressure between the skin and container is relieved, the spring bias of the valve assembly will allow the top member to return to its extended condition and allow the valve to close. Thereafter, the overcap may be replaced.

In the exemplary top member, the presence of the centerbody 54 allows the apertures 50 to be shifted and oriented radially outward to help increase radial distribution of their outlet sprays 320 to more evenly distribute in the volume 310 and the enclosed portion of the skin surface 300. As is discussed below, other configurations are possible.

To assemble the container, the container is manufactured and filled by conventional means. The retention ring is then put in place via depressing to snap engage. The camming surface of its barb initially engages the convex rim of the inner crimp to allow the barb to be driven outward and the retention ring to pass downward. Eventually the barb passes over the crimp and its underside engages the lower rim of the crimp. Further downward motion may be resisted by interaction of the barb's camming surface with the shoulder of the outer member.

With the retention ring in place, the top member may then be put in place. The outer sidewall portion 72 of the retention ring is easily received within the lower portion of the sidewall 32 of the top member. As the top member passes further downward, eventually an upper rim portion of the outer sidewall portion 72 engages the camming surface of the top member sidewall barb. There then may be a combination of inward flexing of the retention ring outer sidewall portion 72 and outward flexing of the top member sidewall 32 to allow further downward passage of the top member. Also, prior to or during this passage, an upper end of the stem 240 passes into/through the lower end of the top member sleeve (which may be beveled to guide insertion).

At approximately the same time/condition: (1) the upper end of the stem will engage the top member webs 52 or outer stop surface; and (2) the barb of the top member sidewall may snap into engagement with the periphery of the shoulder of the retention ring. This essentially simultaneous contact provides positive engagement/positioning of the top member relative to the valve outlet tube and prevents the top member from rattling in its extended condition.

Thereafter, the overcap may be pressed into place.

Figure 6:
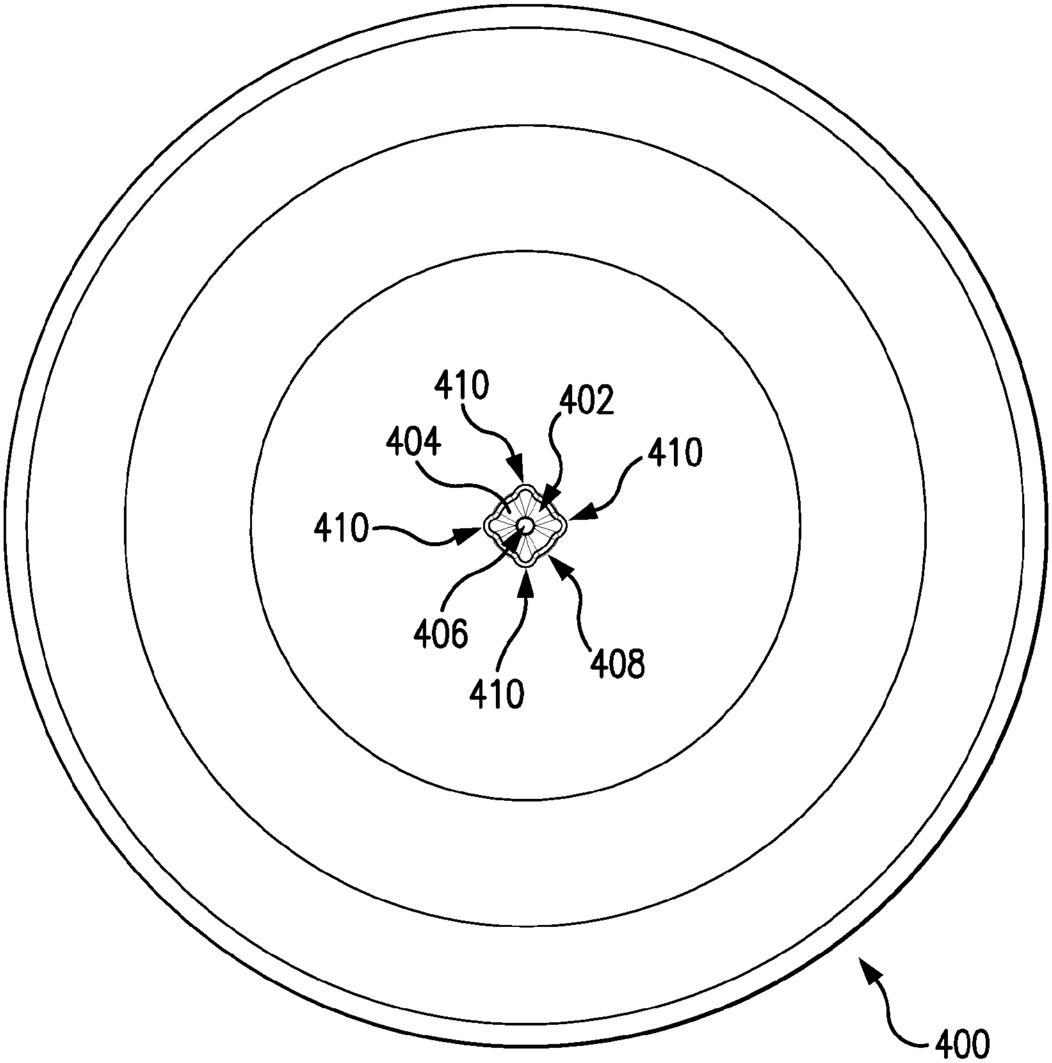
FIG. 6 is a top view of a cup member of an alternate nozzle assembly.

FIG. 6 shows an alternate nozzle differing in that the cup member 400 includes a single central hole 402 and its sleeve (not shown) comprises an annular shoulder abutting the upper rim of the stem 240. The exemplary hole 402 comprises an upwardly divergent surface 404 extending from a lower inlet 406 to an upper outlet 408. The surface 404 has a series of radially extended areas 410 to help radially fan/disperse the spray discharged from the outlet.

One or more embodiments of the present invention have been described. Nevertheless, it will be understood that various modifications may be made without departing from the spirit and scope of the invention. For example, ergonomic modifications and modifications for use with particular bottles (cans) (e.g., other valves, including female valves and other can geometries) may be made. Accordingly, other embodiments are within the scope of the following claims.

What is claimed is:

1. A spray apparatus comprising:
a container; and
a nozzle assembly comprising:
a cup member having:
a central concave surface;
a hole open to the central concave surface;
a conduit extending downward below the hole and cooperating with the container to allow depression of the cup member from a first condition to a second condition to, in turn, pass product from the container out the hole; and
a cup member sidewall; and
a retention ring having:
an inner portion secured to a the container; and
an outer portion cooperating with the cup member sidewall to resist upward movement of the cup member beyond the first condition, the outer portion of the retention ring cooperating with the cup member to guide movement of the cup member during the depression of the cup member from the first condition to the second condition so that the depression of the cup member is depression relative to the retention ring.

2. The apparatus of claim 1 further comprising:
a valve assembly coupled to the conduit.

3. The apparatus of claim 2 wherein:
the valve assembly is a male valve assembly and the conduit is a sleeve receiving an outlet stem of the valve assembly.

4. The system of claim 1 wherein:
the container comprises a metallic can containing a body of the product to be dispensed.

5. The system of claim 1 further comprising:
a removable overcap.

6. The system of claim 1 wherein:
a body of the product within the container comprises at least one of an antiperspirant and a deodorant.

7. The system of claim 1 wherein:
the cup member consists of a single piece plastic molding; and
the retention ring consists of a single piece plastic molding.

8. A method for using the apparatus of claim 1 comprising:
contacting a lip portion of the cup member with skin of a user so that the skin and the cup member define a volume; and
depressing the cup member to discharge a spray of the product from the hole into the volume and onto the skin.

9. The method of claim 8 wherein:
the product applied comprises at least one of an antiperspirant and a deodorant and the skin is along an underarm region.

10. A method for using a spray apparatus, the apparatus comprising a container and a nozzle assembly, the nozzle assembly having a cup member, the method comprising:
contacting a lip portion of the cup member with a skin of the user so that the skin and the cup member define a volume; and
depressing the cup member, the depressing actuating a valve to discharge a spray of the product into the volume and onto the skin.

11. The method of claim 10 wherein:
the product comprises at least one of an antiperspirant and deodorant.

12. The method of claim 10 wherein:
the skin is along an underarm region.

13. The spray apparatus of claim 1 wherein:
the cup member is upwardly open.

14. The spray apparatus of claim 1 wherein:
the container contains a pressurant.

15. The spray apparatus of claim 1 wherein:
the container comprises a valve; and
the cup member cooperates with the valve so that said depression from said first condition to said second condition opens the valve.

16. A spray apparatus comprising:
a container; and
a nozzle assembly comprising:
a cup member consisting of a single piece plastic first molding having:
a central concave surface;
a hole open to the central concave surface;
a conduit extending downward below the hole and cooperating with the container to allow depression of the cup member from a first condition to a second condition to, in turn, pass product from the container out the hole; and
a cup member sidewall; and
a retention ring consisting of a single piece plastic second molding having:
an inner portion secured to the container; and
an outer portion having a surface cooperating with a surface of the cup member sidewall to resist upward movement of the cup member beyond the first condition while allowing downward movement of the cup member relative to the retention ring to the second condition.

17. The spray apparatus of claim 16 wherein:
the retention ring outer portion cooperates with the cup member so that the depression of the cup member is movement relative to the retention ring.

18. A method for using the apparatus of claim 16 comprising:
contacting a lip portion of the cup member with skin of a user so that the skin and the cup member define a volume; and
depressing the cup member to discharge a spray of the product from the hole into the volume and onto the skin.

19. The method of claim 10 wherein the depressing comprises applying force between the container and the skin.

* * * * *